(12) United States Patent
Haeri

(10) Patent No.: US 10,849,659 B2
(45) Date of Patent: Dec. 1, 2020

(54) FERTILITY DEVICE AND METHOD OF USE, OPERATION, AND MANUFACTURE

(71) Applicant: Mikisha Haeri, West Lake Hills, TX (US)

(72) Inventor: Mikisha Haeri, West Lake Hills, TX (US)

(*) Notice: Subject to any disclaimer, the term of this patent is extended or adjusted under 35 U.S.C. 154(b) by 335 days.

(21) Appl. No.: 15/605,252

(22) Filed: May 25, 2017

(65) Prior Publication Data

US 2018/0338779 A1   Nov. 29, 2018

(51) Int. Cl.
*A61B 17/425* (2006.01)
*A61F 5/455* (2006.01)

(52) U.S. Cl.
CPC .......... *A61B 17/425* (2013.01); *A61F 5/4553* (2013.01)

(58) Field of Classification Search
CPC ........ A61B 17/425; A61F 6/08; A61F 5/4553; A61F 13/2045; A61H 19/40–50; A61H 21/00
See application file for complete search history.

(56) References Cited

U.S. PATENT DOCUMENTS

| | | | |
|---|---|---|---|
| 1,280,979 A | 10/1918 | Ellis | |
| 1,790,801 A | 2/1931 | Dickstein | |
| 4,241,912 A | 12/1980 | Mercer et al. | |
| 4,246,901 A | 1/1981 | Michaud | |
| 5,787,891 A | 8/1998 | Sak | |
| 5,827,248 A * | 10/1998 | Crawford | A61F 5/4553 604/328 |
| 5,853,362 A | 12/1998 | Jacobs | |
| 6,230,709 B1 * | 5/2001 | LaVean | A61F 6/08 128/834 |
| 6,370,912 B1 | 4/2002 | Sutton | |
| 6,562,018 B1 | 5/2003 | Russell | |
| 6,676,594 B1 | 1/2004 | Zunker et al. | |
| 6,695,763 B2 | 2/2004 | Zunker et al. | |
| 2004/0089312 A1 | 5/2004 | Jordan | |
| 2005/0028824 A1 | 2/2005 | Jordan et al. | |
| 2009/0095304 A1 * | 4/2009 | Richardson | A61F 2/0009 128/834 |
| 2015/0359684 A1 * | 12/2015 | Strong | A61F 13/2085 28/120 |
| 2018/0014854 A1 * | 1/2018 | Souther | A61B 17/43 |
| 2019/0224039 A1 * | 7/2019 | Garriga I Rodo | A61F 5/4553 |

* cited by examiner

*Primary Examiner* — Thaddeus B Cox
(74) *Attorney, Agent, or Firm* — Pillsbury Winthrop Shaw Pittman, LLP

(57) ABSTRACT

Provided is a fertility device configured to be placed into a subject's vagina after intercourse, the fertility device comprising: a vaginal portion, the vaginal portion comprising: a proximal end; a distal end opposite the proximal end along a longitudinal axis; and a middle portion between the proximal and the distal end; and a lead operatively coupled to the proximal end, wherein: when at least part of the middle portion is placed into a subject's vagina, the lead remains partially outside the vagina, and the vaginal portion impedes leakage of sperm.

24 Claims, 6 Drawing Sheets

FERTILITY DEVICE AND METHOD OF USE, OPERATION, AND MANUFACTURE

BACKGROUND

1. Field

The present disclosure relates generally to medical devices and, more specifically, to vaginally inserted medical devices having application in the field of fertility.

2. Description of the Related Art

Couples trying to conceive a baby often seek to improve their chances of conception. Generally, about 80% of couples who try to conceive are successful during the first six months. About 90% of couples are able to conceive during the first year. In some cases, during the pre-conception period, some couples may experience anxiety about their ability to conceive. Often, many women trying to conceive attempt to hold semen inside their vagina as long as they can after intercourse to increase their chances of conception. Some try to stay in the same position (e.g., lying down after intercourse) with their pelvis elevated for a period of time to keep semen inside for a period long enough to allow the semen to travel to the uterus. In some cases, women may use some type of support under their lower back (e.g., pillows, or wedges) to elevate their vagina to optimize the chance of the sperm reaching the uterus to start the fertilization process.

The traditional ways of keeping sperm inside the vagina after intercourse is often not very practical, since most require women to stay in bed, or in a specific position for a long period of time. During this time women are generally not able to do other activities (e.g., stand up, walk, shower, etc.) Accordingly, there is a need for a more practical solution to help women hold semen in their vaginas.

SUMMARY

The following is a non-exhaustive listing of some aspects of the present techniques. These and other aspects are described in the following disclosure.

Some aspects include a fertility device configured to be placed into a subject's vagina after intercourse, the fertility device comprising: a vaginal portion, the vaginal portion comprising: a proximal end; a distal end opposite the proximal end along a longitudinal axis; and a middle portion between the proximal and the distal end; and a lead operatively coupled to the proximal end, wherein: when at least part of the middle portion is placed into a subject's vagina, the lead remains partially outside the vagina, and the vaginal portion impedes leakage of sperm from the vagina.

Some aspects include a process of using the above fertility device.

Some aspects include a process of operating the above fertility device.

Some aspects include a process of manufacturing the above fertility device.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
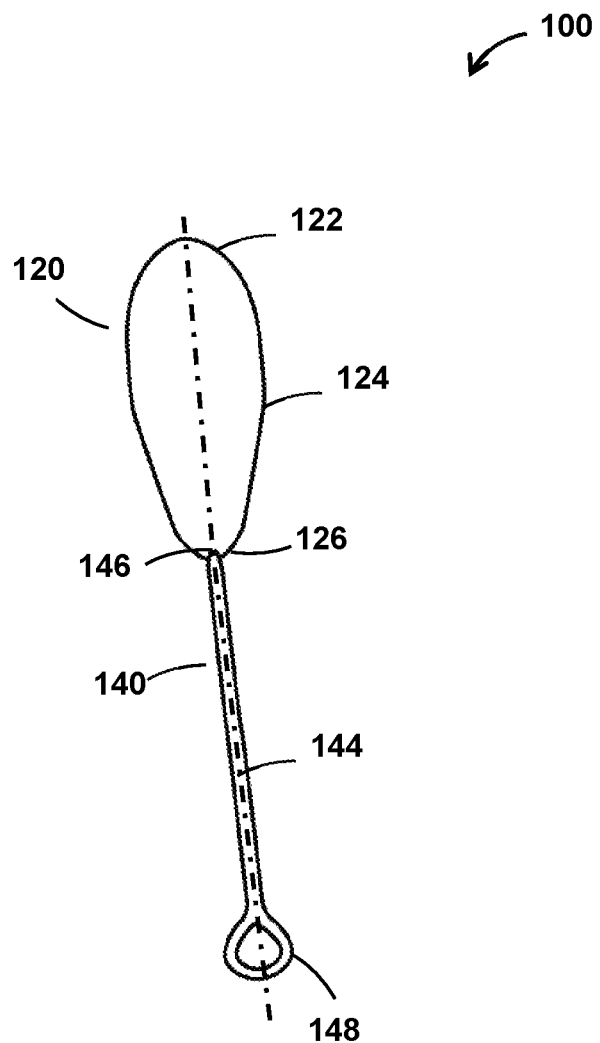
FIG. 1 is an occluded line plan view that illustrates an example of a fertility device, in accordance with some embodiments.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the field of fertility. Indeed, the inventors wish to emphasize the difficulty of recognizing those problems that are nascent and will become much more apparent in the future should trends in the data center industry continue as applicants expect. Further, because multiple problems are addressed, it should be understood that some embodiments are problem-specific, and not all embodiments address every problem with traditional methods of treating fertility described herein or provide every benefit described herein. That said, improvements that solve various permutations of these problems are described below.

Some of the above-mentioned issues (and others discussed below and that will be apparent to those of skill in the art) may be mitigated with one of the fertility devices illustrated in FIGS. 1-6. Generally, the typical lifespan of sperm in a woman's body after intercourse is between a few hours and up to five days. Typically, the longer the sperm stays in the woman's body, the higher the chances of the sperm reaching the uterus and, thus, the higher the chance of fertilization. Some embodiments may provide a practical approach that is relatively inexpensive, relatively easy to use, and that is expected to help women (users) increase the amount of semen retained in their vagina after intercourse, without impeding other daily activities or routines (e.g., showering, exercising, working, etc.) In some embodiments, the fertility device may be held in place for a few minutes, an hour, a plurality of hours, or longer in some cases.

Some embodiments may allow the user to put the fertility device in place in their vagina (or vaginal canal) through the vaginal opening after intercourse and go on with their daily activities without having to stay in bed to try to keep the semen in their vagina. For example, fertility device 100 of FIG. 1 is configured to be placed into the vaginal canal (via the vaginal opening) after intercourse. For example, the woman may place the fertility device 100 into the vaginal canal while lying down after intercourse to facilitate insertion and while the semen is still in the vagina. Or, the fertility device may be put in place while the woman is in a different position (e.g., standing, kneeling, etc.). The fertility device is expected to prevent or impede semen from leaking from the woman's vagina, thereby increasing the chances for the semen to reach the uterus. While "wearing" the fertility device, the woman is expected to be able to do her daily activities without interruption (e.g., showering, working, exercising, etc.)

In some embodiments, fertility device 100 of FIG. 1 includes a vaginal portion 120 and lead 140. In some embodiments, vaginal portion 120 may be generally rotationally symmetrical about axis A, e.g., concentric about axis A. In some cases, a cross section normal to the axis A may be circular or ellipsoidal, or another shape for which the vaginal portion 120 is insert-able in the vagina (or vaginal canal) comfortably, e.g., a Reuleaux triangle. Lead 140 may similarly be rotationally symmetric, may have a cross sectional area (normal to axis A) that is less than 50% (e.g., less than 20% or less than 10%) that of the vaginal portion 120 (e.g., at their respective widest or narrowest points). Lead 140 and may be coupled to the vaginal portion 120 as described below.

In some embodiments, vaginal portion 120 includes a distal end 122, a proximal end 126 (proximal to, e.g., directly connected to, lead 140) opposite distal end 122 along a longitudinal axis A, and a middle section 124. The middle section 124 may lie between and couple the distal end and the proximal end 126 to one another. In some cases, these components 122, 126, and 124 may be seamlessly joined to one another and parts of a monolithic body.

The distal end 122 may be rotationally symmetric about axis A and may have, for instance, an ogive cone, a spherically blunted cone, an elliptical cone, a parabolic cone, a conical shape, or frustum shape, e.g., with a circular or ellipsoidal cross section normal to axis A that decreases in area (e.g., monolithically, such as linearly or non-linearly) from the middle section 124 to the furthest point of the device 100 along axis A. In some cases, a radius of the cross section may decrease along a linear path, a parabolic path, or a circular arc along the axis A. In some cases, the distal end 122 may be reflectively symmetric about a plane in which axis A lies, e.g., where the cross section normal to axis A is circular or an ellipse. In some cases, the distal end 122 may account for between 5 and 80% of the length of the vagal portion 120 along axis A, e.g., between 10 and 40%. In some cases, a largest dimension of the distal end 122 normal to, and extending from, the axis A (e.g., a radius of a circle or semi-major axis of an ellipse) is between 0.5 and 3 cm.

The middle section 124 may also be rotationally symmetric about axis A and reflectively symmetric about a plane in which axis A lies, e.g., with a circular or ellipsoidal cross section normal to axis A. The middle section may have a constant cross sectional area normal to the axis A (e.g., substantially constant, for instance varying by less than 5%). Or in some case, the cross sectional area of the middle section may vary along axis A as discussed below with reference to FIGS. 2-6. In some cases, the middle section 124 may account for between 5 and 80% of the length of the vagal portion 120 along axis A, e.g., between 10 and 40%. In some cases, a largest dimension of the middle section 124 normal to and extending from the axis A (e.g., a radius of a circle or semi-major axis of an ellipse) is between 0.5 and 3 cm. In some cases, the middle section 124 has a cross sectional area normal to axis A that is larger than or equal to a largest cross sectional area of the distal end 122 and the proximal portion 126.

The proximal portion 126 may also be rotationally symmetric about axis A and may have, for instance, an ogive cone, a spherically blunted cone, an elliptical cone, a parabolic cone, a conical shape, or frustum shape, e.g., with a circular or ellipsoidal cross section normal to axis A that decreases in area (e.g., monolithically, such as linearly or non-linearly) from the middle section 124 to the closest point of the device 100 along axis A to the lead 140. In some cases, a radius of the cross section may decrease along a linear path, a parabolic path, or a circular arc along the axis A, in a direction opposite that of the distal end 122. In some cases, the proximal portion 126 may be reflectively symmetric about a plane in which axis A lies, e.g., where the cross section normal to axis A is circular or an ellipse. In some cases, the proximal portion 126 may account for between 5 and 80% of the length of the vagal portion 120 along axis A, e.g., between 10 and 40%. In some cases, a largest dimension of the proximal portion 126 normal to and extending from the axis A (e.g., a radius of a circle or semi-major axis of an ellipse) is between 0.5 and 3 cm.

In some embodiments, vaginal portion 120 is coupled to lead 140 at proximal end 126. In some embodiments, the distance between the distal end 122 and the proximal end (e.g., from their furthermost parts) is longer than 2 cm and less than 10 cm, e.g., between 4 and 6 cm.

In some embodiments, lead 140 includes an elongated portion 144 and an end portion 148. Elongated portion 144 may extend from vaginal portion 120 to end portion 148. In some cases, lead 140 may have a length that ranges approximately between 5 and 20 cm (two and eight inches). In some embodiments, lead 140 may also be rotationally symmetric about axis A and reflectively symmetric about a plane in which axis A lies, e.g., with a circular or ellipsoidal cross section normal to axis A. In some embodiments, end portion 148 has a generally spherical shape and a wider cross sectional area than elongated portion 144 to facilitate gripping the end portion 148 and placing the elongated portion 144 in tension to apply a pulling force to the device 100.

In some cases, one or both of the vaginal portion 120 and lead 140 are made from (e.g., exclusively or partially (e.g., fully externally covered with)) a relatively flexible material (e.g., with a Young's modulus of less than 4 GPa, less than 2 GPa, less than 0.5 Gpa, or less than 0.05 Gpa). A flexible material is expected to be easily inserted into the vagina and feel comfortable to keep while doing other activities (e.g., in some embodiments, lead 140 is flexible, discrete and can be comfortably used with an underwear or other clothing), though embodiments are not limited to devices providing this benefit, as multiple independently useful techniques are described with different engineering and cost tradeoffs, which is not to suggest that any other description is limiting.

In some embodiments, fertility device 100 may be made of (e.g., coated with or entirely made of, like as a monolithic body) a variety of materials or combinations of material. In some embodiments, fertility device 100 may be made of medical grade silicone. Medical grade silicone is generally known for its softness and ease of care. This is expected to make caring and storing of fertility device 100 easy. For example, rinsing fertility device 100 with water and soap before (or after) use may all that is needed to be done to clean the fertility device (e.g., no sterilization or special storage needed.) Alternatively, or additionally, fertility device 100 may be made of latex, rubber, polycarbonate, methyl methacrylate, polyurethanes, glass, acrylic, or plastic, e.g., either alone or in combination. In some cases, vaginal portion 120, and lead 140 are made out of different materials.

In some embodiments, the vaginal portion 120 or the lead 140 are constructed such (e.g., due to material choice or internal cavities, or both) that under a force or pressure (e.g., radially inward) vaginal portion 120 or lead 140 may relatively change shape, and return to their original shape when the force is not applied anymore. For example, vaginal portion 120 (or lead 140) may be relatively deformed to a degree to allow for insertion into the vagina. This can be the result of a force or a pressure applied by the woman (e.g., using her fingers, or hand). The force may be applied to the vaginal portion 120 (or lead 140) before it is inserted into the vagina (e.g., the woman squeezes the vaginal portion before inserting it into the vagina). In some embodiments, the force or pressure may be applied to vaginal portion 120 as a result of the insertion (e.g., the opening of the vagina may apply a force on the vaginal portion while the vaginal portion is being inserted causing the vaginal portion 120 to relatively deform temporarily from its original shape). In some embodiments, the inner walls of the vagina apply a force on portions of the vaginal portion 120 (that is inserted into the vagina) that causes the vaginal portion 120 to relatively deform temporarily. In some embodiments, once the force or pressure is stopped, the vaginal portion 120 or lead 140 returns to (or closer to) its original shape. That said, the present techniques are consistent with a fertility device that may stay deformed or do not deform as a result of the applied force or pressure, which is not to imply that other descriptions are limiting.

In some embodiments, fertility device 100 may be manufactured as an integral unit (using injection molding for example to form a monolithic body in a single mold cavity). In some embodiments, different parts of fertility device 100 may be manufactured separately (e.g., vaginal portion 120 and lead portion may be manufactured separately and operatively coupled together to form fertility device 100.) In some embodiments, the fertility device 100 may include an internal cavity (such as sealed chamber or chamber with a venting hole) to make the outer shape more resilient, or the fertility device 100 may be solid throughout. Internal cavities may be formed with a variety of techniques, including with an insert in an injection molding process, or by separately molding two halves (e.g., split on a plane along the longitudinal axis of the device 100) and joining the two halves (e.g., with an adhesive or fusing with heat). In some cases, fertility device 100 may be made from a thermoset or a thermoplastic polymer. In some cases, two components of a thermoset polymer may be combined as a liquid and poured into a mold in which the components are left to cure through a cross linking or chain extension chemical process.

In operation, in some embodiments, when placed in the woman's vagina, the portion of the vaginal portion 120 opposite the lead 140 is inserted into the vaginal canal (e.g., at least part of the vaginal portion 120 or all of vaginal portion 120), and lead 140 remains outside the woman's body (e.g., at least part of the lead 140 or all of the lead 140 remains outside).

With ejaculation of semen, a high number of sperm reach the cervix, and after ejaculation (e.g., a few minutes after ejaculation), sperm begin to swim into the cervical mucus of the cervix and through microscopic tubes in the uterus to reach an unfertilized egg in the fallopian tube. Generally, the vagina is an acidic environment that is very harsh for the sperm (acidity generally kills sperm). Therefore, the quicker the sperm reach the cervix (the cervix mucus is generally alkaline which help the sperm survive) and the uterus the higher their chances of survival and the higher the chance of an egg to be fertilized. Sperm that have not penetrated the cervical mucus quickly (around half an hour after ejaculation) lose their ability to swim to the alkaline environment of the cervix. Additionally, sperm that is left in the semen usually deteriorate after about two hours. Fertility device 100 is expected to help the sperm reach the cervix by preventing the semen from leaking from the vagina. For example, fertility device may be configured to reach the cervix opening when inserted in the vagina, thereby allowing a high number of sperm to reach the cervix quickly and preventing the sperm from going down the vagina where they may not survive.

In some embodiments, upon being inserted, the exterior surface of the vaginal portion 124 may form a partial or full seal against the vaginal canal that impedes or prevents semen from escaping, e.g., impeding semen flow out of the vagina to less than 1 ml per minute, less than 1 ml per hour, or less than 1 ml per day. In some cases, the vaginal portion 120 may elastically push radially outward against the vaginal canal, placing the vaginal portion 120 in compression and the vaginal canal in tension to form a better seal. Generally, the vagina is an elastic muscular canal extending from the vaginal opening to the cervix (entrance of the uterus) for about three to six inches. The vagina expends in length and width with sexual arousal in general. The length of the vagina may be different for different women (e.g., depending on their age, ethnicity, etc.) The uterus is a pear-shaped structure that connects to the vagina via the cervix. The cervix has a triangular cavity inside, where the fertilized egg grows. The uterus includes microscopic tubes through which the sperm passes to reach the fallopian tubes, where it may meet an unfertilized egg (The ovaries are the organs that make the female's eggs.)

The portion of lead 140 outside of the woman's body may provide an interface by which the fertility device 100 is removed, e.g., by pulling on the lead 140. For instance, in some embodiments, the woman may remove the fertility device from her vagina relatively easily by gently pulling on lead 140. To facilitate movement of the woman while wearing the device 100, the lead 140 may be substantially more flexible than the vaginal portion 120. For instance, a bending force applied equidistance between two supports normal to the axis A may yield more than 30%, more than 50%, or more than 200% more translation at the point where the force is applied in the lead 140 than in the vaginal portion 120. Thus, the lead 140 may flex and permit movement while the vaginal portion 120 maintains its shape and seal to a greater degree.

After use, in some embodiments, fertility device 100 may be washed with water and soap and stored, in some cases, with no need to special cleaning procedures or special storage. (That said, in some cases consistent with the present techniques, fertility device 100 may be disinfected, sanitized, or sterilized (e.g., using heat, radiation or chemical based techniques) depending on the material used to manufacture the fertility device or depending on the need of the user.) In some embodiments, the fertility device may retain less than 1 ml of water upon being immersed in a water bath for an hour and hand dried with a towel.

In some cases, fertility device 100 may be used to apply ointment, medicine, or other preparations (medicinal or non-medicinal) inside the vagina, the cervix, or the uterus. For example, an ointment or other preparation may be placed on fertility device 100 on a n outer surface of the device (e.g., on the top end, or on the sides), and as fertility device 100 is inserted into the woman's vagina, the preparation is applied to the walls of the vagina, the cervix, or the uterus. This is expected to facilitate application of the preparations and help hold them in place. In some embodiments, the preparation may be applied by the woman and the fertility device 100 may be used to keep the preparation from leaving the vagina. For example, the woman may put a suppository (or other medicine, or device) in place and use fertility device 100 afterwards to hold the suppository (or other medicine, or device) in place. In some embodiments, when used for preparations delivery (e.g., medicine, ointment, gel, etc.) vaginal portion 120 may have a concave surface on the top end configured to receive the preparations to be delivered. Similarly, these embodiments are expected to allow the woman to carry on with her regular activities with minimal interruptions.

Figure 2:
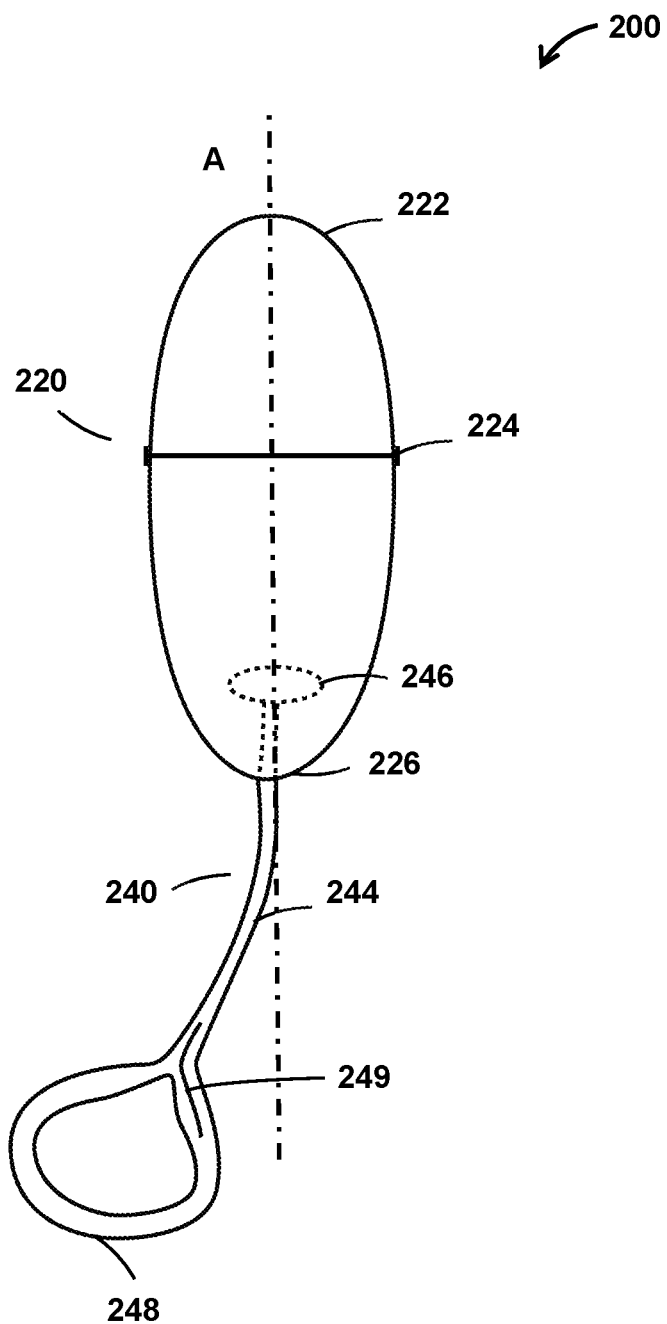
FIG. 2 is a hidden line plan view that illustrates an example fertility device, in accordance with some embodiments.

FIGS. 1-2 show an example of vaginal portion 120 having a generally elliptical shape (in the plan view, which is distinct from, though compatible with, an elliptical shape in cross sectional area normal to axis A) with distal end 122 having a rounded tapered shape to facilitate insertion into the vagina. In some embodiments, the length of vaginal portion 120 (distance between distal end 122 and proximal end 126) may range between approximately five and 12 cm (or two and 4.7 inches). In some embodiments, a diameter of vaginal portion 120 (diameter of the widest section of the elliptical shape for example middle section 124) may range between approximately one and 8.9 cm (or 0.39 and 3.5 inches). It is to be understood that these ranges are only examples, vaginal portion 120 may have different dimensions (length, or diameter) at different points of vaginal 120 (e.g., along axis A), which is not to imply that other descriptions are limiting. As can be seen in FIG. 1, in some embodiments, vaginal portion 120 tapers from middle section 124 towards distal end 122 such that a diameter of the vaginal portion 120 near distal end 122 is smaller than the dimeter at middle section 124. For example, diameter of distal end 122 may be around two cm (or about 0.8 inches), and diameter of the middle portion 124 may be around 2.5 cm (or around one inch) in some cases. In some embodiments, vaginal portion 120 also tapers from middle section 124 towards proximal end 126 such that a diameter of the vaginal portion 120 near proximal end 126 is smaller than the dimeter at middle section 124. In some cases, the diameter of vaginal portion 120 at proximal end 126 reduces to a point of contact between vaginal portion 120 and lead 140 (e.g., reduces to a width or diameter of lead 140.)

In some embodiments, fertility device 100 may be inserted into the vagina such the vaginal portion 120 reaches the woman cervix. For examples, the woman may insert fertility device until vaginal portion naturally stops because it reached the cervix, or the woman may stop when she feels that vaginal portion reached the cervix. In some cases, fertility device 100 may be placed at any depth position (along the length of the vagina). For example, half way to the cervix, two thirds of the way to the cervix, or at any depth. For example, some women may feel more comfortable with the fertility device inserted two thirds of the way to the cervix (e.g., as long as proximal end 126 of vaginal portion is within the vagina or at the vagina opening.)

In some embodiments, vaginal portion 120 has a flexible construction and is made from a supple material that is able to compress for easy insertion and able to return back into shape (e.g., after insertion, or after removal). For example, vaginal portion 120 may be deformable (e.g., made from an elastomer polymer) that compresses to a certain degree to allow the user to place vaginal portion 120 into the vaginal canal without difficulty. Once inserted, vaginal portion 120 returns to its original shape to relatively fill the vaginal canal. In some embodiments, vaginal portion 120 may include an interior empty cavity that creates a hollow portion within vaginal portion 120. For example, the cavity may be located in about the center of the vaginal portion 120 (or in other locations within the vaginal portion). A vaginal portion 120 including a cavity may be advantageous for its relatively highly flexibility, light weight, and low manufacturing cost (e.g., less material needed.).

In some embodiments fertility device 100 may be constructed to relatively seal the vaginal canal to provide a near seal of the vaginal canal thus preventing or impeding leakage of the sperm from the vagina. For example, in some cases the fertility device may be operative to retain about 90% of the sperm while in use for a period of time (e.g., the period of time can be few minutes up to few hours, or less than few minutes). In some cases, the fertility device may be operative to retain up to 90% of the sperm. In some embodiments, the fertility device may be operative to retain more than 90% of the sperm. It is to be understood that the percentage of impedance and the duration of time are given here as examples only, other combinations of percentage and/or duration of time may be considered and are consistent with the present techniques, which is not to imply that other descriptions are limiting.

In some cases, vaginal portion may be configured to conform to the shape of the vaginal canal (e.g., to fit ridges inside on the vaginal canal). In some embodiments, the fertility device may include one or more texturized portions to help keep the vaginal portion 120 in place. In some cases, vaginal portion 120 may be constructed to follow the shape of the user's vagina. For example, different women may have different shape vaginas, vagina openings, and canals. For example, a vagina may have a pear, conical, parallel sided shapes, or other shapes. In some embodiment, the user's vaginal measurements (e.g., taken from an ultrasound or MRI image, a cast, or by a measuring device), may be used to construct a personalized fertility device 100. In some embodiments, the personalized fertility device may be on demand 3D printed. This is expected to produce a personalized fertility device that fits the user's vagina, hence providing a strong protection against sperm leakage.

That said, in some embodiments, vaginal portion 120 does not need to be flexible to be placed in the woman's vagina (for example, in some cases, vaginal portion 120 has a relatively rigid construction (e.g., relatively non-compressible.) Generally, during intercourse the walls of the vagina expand and lubricate which may reduce friction when inserting fertility device into the vagina after sexual activity. In some cases, a lubricant (e.g., water based) may be used to help insertion of the fertility device and is consistent with one or more embodiments of the present techniques. In these embodiments, for example, vaginal portion 120 may be of rigid construction and lead 140 may be of a supple flexible construction to allow the woman to get up, walk, shower, etc. with the rigid part of the fertility device vaginal portion 120 is inside the vagina and the flexible part (lead 140) remains outside the vagina. In some cases, vaginal portion and lead 140 may have a rigid construction. In these cases, the woman may choose to remain in a position that is comfortable for her to keep the fertility device in place (e.g., laying down) or may choose to get up and do some activities while having the fertility device inside her vagina (e.g., the woman may take a shower with the relatively rigid fertility device inside her vagina since this activity does not require clothing.)

In some embodiments, vaginal portion 120 may be made from medical grade chemically inert materials that are easy to clean, maintain, and store. For example, such materials may include silicone, latex, rubber, polycarbonate, methyl methacrylate, polyurethanes, glass, acrylic, plastic, or any combination thereof. For example, in some embodiments, medical grade silicone may be used to manufacture some or all parts of fertility device 100. Medical grade silicone may be advantageous in some embodiments, because it is durable, soft and lacks harmful chemicals. In some embodiments, latex may be used to form some or all parts of fertility device 100 to provide a soft non-porous surface that is easy to be inserted into the vaginal cavity and is comfortable for the user to wear for extended periods of time. Latex is generally non-toxic and is easy to clean (e.g., soap and water). In some embodiments, acrylic may be used for example where the vaginal portion 120 is of relatively rigid construction. Acrylic is expected to provide a smooth non-toxic surface that is non-porous and is easy to store and to clean. In some embodiments, vaginal portion 120 may be made of plastic. Plastic may be advantageous in some cases, for its lightweight and low cost.

In some embodiments, lead 140 is configured to facilitate insertion or removal of fertility device 100 from the vagina. Lead 140 is configured to extend from vaginal portion 120 (e.g., from proximal end 126) and remains outside (e.g., at least partially outside) of the body of the woman when the fertility device is inside (e.g., at least partially inside) the vagina, in some cases. In some embodiments, device 100 may be removed from the vagina by applying a gentle pulling force to lead 140. In some embodiments, lead 140 may partially remain outside of the body, with portions of the lead being inside the vagina.

In some embodiments, lead 140 may be formed from the same material as vaginal portion 120 (e.g., silicone, latex, rubber, polycarbonate, methyl methacrylate, polyurethanes, glass, acrylic, plastic, or any combination thereof). In some embodiments, lead 140 and vaginal portion 120 are manufactured as an integral unit (e.g., using injection molding, or 3D printing.) In some embodiments, lead 140 may be made out of (e.g., reinforced cotton, nylon, satin, polypropylene thread, woven fibers, etc.) In some embodiments, lead 140 may include an embedded filament (similar to filament 249 shown and described with respect to FIG. 2) configured to reinforce and add strength to lead 140

In some embodiments, lead 140 may be operatively coupled to vaginal portion 120. For example, lead 140 may be anchored within vaginal portion 120 at anchor 146 during the manufacturing process. For example, vaginal portion 120 may have a small opening about proximal end 126, the opening being configured to receive anchor 146 of elongated portion 144 of lead 140. Elongated portion 144 may be anchored to vaginal portion 120 using heat or glue for example. In some embodiments, anchor 146 may be in the form a reinforcement point to prevent lead 140 from breaking off of fertility device 100. For example, in the case where lead 140 is manufactured separately from vaginal portion 120, anchor 146 may be in the form of a ball (or other shape) that fits snugly within vaginal portion 120 and that prevents lead 140 from breaking off vaginal portion 120. In other cases, where fertility device is manufactured as an integral unit, a reinforcement point may be created at anchor 146 during manufacturing (e.g., in injection molding an anchor may be placed in the mold during the manufacturing process.)

Figure 5:
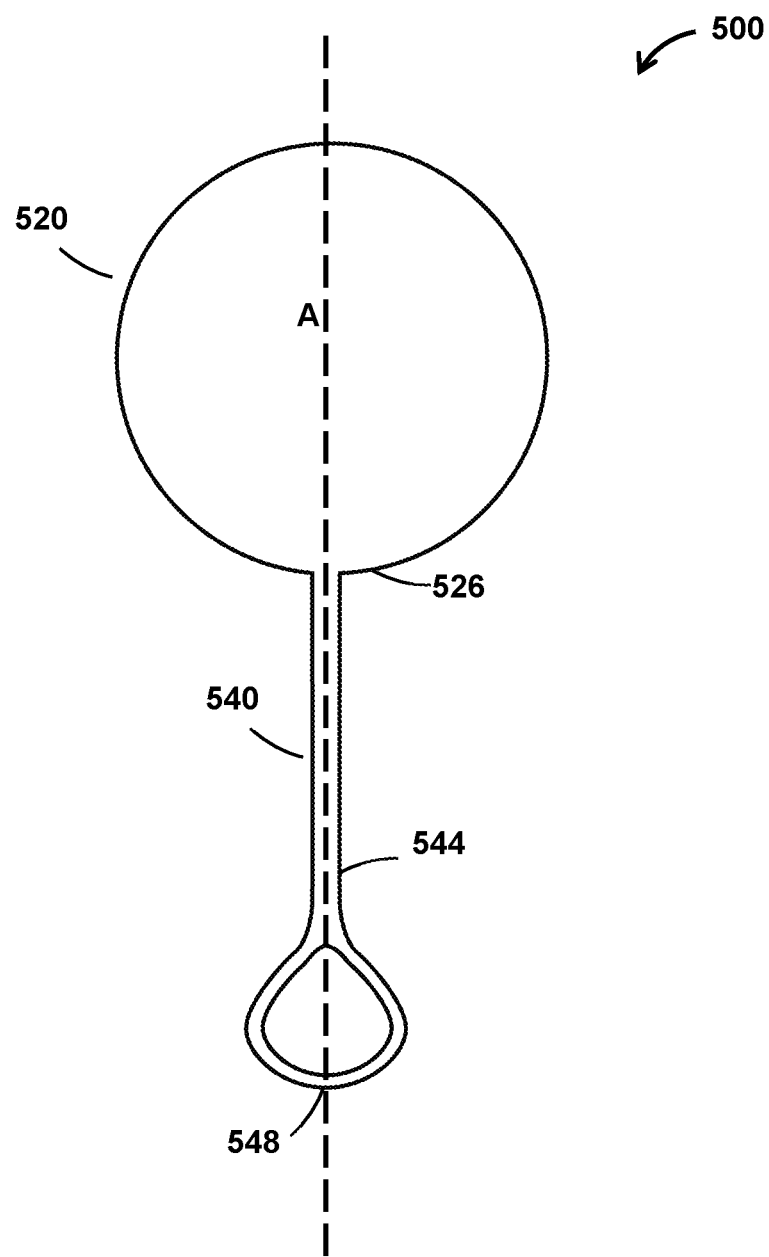
FIG. 5 is a hidden line plan view that illustrates an example fertility device, in accordance with some embodiments.

End portion 148 is configured to facilitate removal or insertion of fertility device 100. In some embodiments, end portion 148 of lead 140 may be in the form of a small ball, or other small volume shape that is relatively bigger than the diameter of the elongated portion 144. In some embodiments (as also shown in FIGS. 2 and 5), elongated portion may form a small ring (with a relatively circle shape) at end portion 148 to allow a finger (in some cases more than one finger) to be inserted into end 148 to facilitate pulling of lead 140 (or other manipulation of lead 140). In some embodiments, end portion 148 is an integral part of lead 140 (e.g., manufactured as an integral unit). In other cases, end portion 148 is operatively coupled to lead 140.

FIG. 2 describes an example of fertility plug 200 according to some embodiments. In this example, vaginal portion 220 has a generally elliptical shape (in the plan view, which is distinct from, though compatible with, an elliptical shape in cross sectional area normal to axis A). In some embodiments, vaginal portion 220 includes a distal end 222, and a proximal end 226 (proximal to lead 240) opposite distal end 222 along an axis A. In some embodiments, vaginal portion 220 is coupled to lead 240 at proximal end 226. In some cases, vaginal portion 220 and lead 240 are constructed as an integral unit. In some cases, vaginal portion 220 and lead 240 are configured to be operatively coupled together.

In some embodiments, the length of vaginal portion 220 (distance between distal end 222 and proximal end 226) may range between approximately five and 22 cm (or two and 4.7 inches). In some embodiments, a diameter of vaginal portion 220 (diameter of the widest section of the elliptical shape for example middle section 224) may range between approximately one and 8.9 cm (or 0.39 and 3.5 inches). It is to be understood that these ranges are only examples, vaginal portion 220 may have different dimensions (length, or diameter) at different points of vaginal 220 (e.g., along axis A), which is not to imply that other descriptions are limiting. As can be seen in FIG. 2, in some embodiments, vaginal portion 220 tapers from middle section 224 towards distal end 222 such that a diameter of the vaginal portion 220 near distal end 222 is smaller than the dimeter at middle section 224. For example, diameter of distal end 222 may be around two cm (or about 0.8 inches), and diameter of the middle portion 224 may be around 2.5 cm (or around one inch) in some cases. In some embodiments, vaginal portion 220 also tapers from middle section 224 towards proximal end 226 such that a diameter of the vaginal portion 220 near proximal end 226 is smaller than the dimeter at middle section 224.

In some embodiments, lead 240 includes an elongated portion 244 and an end portion 248. Elongated portion 244 extends from proximal end 226 of vaginal portion 220 to end portion 248 of the Lead 240 is configured to facilitate removal of fertility device 200 from the vagina by applying a pulling force to lead 240. In some embodiments, end portion 248 may be configured to receive a finger (or more than a finger in some cases) to facilitate manipulation of the lead 240 or fertility device 200. End portion 248 may have different forms/shapes (e.g., ring shape, loop shape, or a volume with an aperture to receive one or more fingers.) In some embodiments, lead 240 may be formed from the same material as vaginal portion 220 (e.g., silicone, latex, rubber, polycarbonate, methyl methacrylate, polyurethanes, glass, acrylic, plastic, or any combination thereof). In some embodiments, lead 240 and vaginal portion are manufactured as an integral unit (e.g., using injection molding, or 3D printing.)

In some embodiments, lead 240 may include an embedded filament 249 configured to reinforce and add strength to lead 240. The embedded filament 249 may be embedded during the injection molding for example. The embedded filament 249 may be made out of a variety of different types of durable material (e.g., metal, plastic, woven fibers, etc.). In some embodiments, embedded filament 249 may be placed one or more portions of lead 240. For example, embedded filament 249 may be placed along elongated portion 244 such that a first end of filament 249 is near or at anchor 246 of vaginal portion 220 and the other end (opposite the first end) is near or at end portion 248. In some embodiments, end portion 248 may be filled with a reinforcing material to add a small weight to help keep the end portion 248 outside of the woman vagina. In some embodiments, vaginal portion 120 may include one or more portions of embedded filament 249. For example, in some cases, embedded filament 149 follows the shape of vaginal portion 220.

Figure 3:
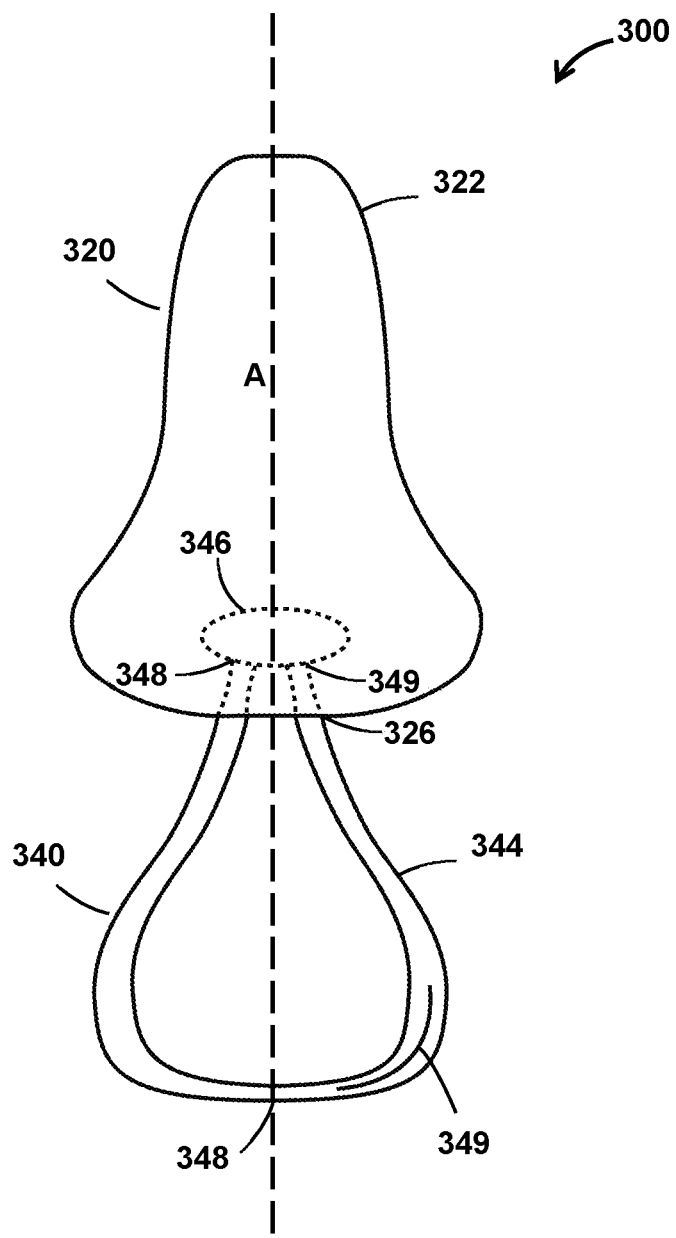
FIG. 3 is a hidden line plan view that illustrates an example fertility device, in accordance with some embodiments.

FIG. 3 illustrates an example of fertility device 300 according to some embodiments. Fertility device 300 includes vaginal portion 322 and lead 340. Vaginal portion 320 has a generally pear shape with distal end 322 having a rounded tapered shape to facilitate insertion into the vagina. Vaginal portion 320 tapers from proximal end 326 towards distal end 322 such that a diameter of the vaginal portion 320 near distal end 322 is smaller than the dimeter of vaginal portion 320 at proximal end 326. In some embodiments, proximal end 326 forms a base for vaginal portion 320 (having a diameter of about 3.5 cm) configured to remain outside the vagina when vaginal portion 320 is inserted into the vagina. For example, proximal end 326 (base) may be configured to relatively close the opening of the vagina while remaining outside of the vagina. In some embodiments, proximal end 326 (base) may be inserted into the vagina and relatively close the opening of the vagina from inside the vagina to prevent sperm from leaking from the vagina. In some embodiments, the length of vaginal portion 320 (distance between distal end 322 and proximal end 326) may range between approximately five and 12 cm (or two and 4.7 inches). In some embodiments, a diameter of vaginal portion 320 at distal end 322 may range between one and three cm. In some embodiments, a diameter of vaginal portion 320 at proximal end 326 may range between 2.5 and 3.8 cm. It is to be understood that these ranges are only examples and that other dimensions are consistent with the present techniques, which is not to imply that other descriptions are limiting.

Lead 340 includes an elongated portion 344. In some embodiments, lead portion 340 may be similar to lead 140 described above. In some embodiments, elongated portion 344 may form a loop having a first end 348 and a second end 347. Loop 344 is expected to facilitate removal or insertion of fertility device 300 by acting like a handle where the woman may place more one or more fingers to manipulate the fertility device. In some embodiments, loop 344 may hang from fertility device 300 by about two to six inches. Loop 344 extends from end 348 (located near proximal end 326 of vaginal portion 320 at or near anchor 346) to end portion 347 (also located near proximal end 326 of vaginal portion 320 at or near anchor 346).

In some embodiments, lead 340 may include embedded filament 349 for reinforcement. The embedded filament 349 may be embedded during of lead 340 or manufacturing of fertility device 300 for example. The embedded filament 349 may be made out of any type of durable material (e.g., metal, plastic, woven fibers, etc.) In some embodiments, embedded filament 349 may be placed in one or more portions of lead 340. For example, embedded filament 349 may be placed along elongated portion 344 such that a first end and a second end of filament 349 are near or at anchor 346 of vaginal portion 320. In some embodiments, vaginal portion 320 may include one or more portions of embedded filament (e.g., that follows the shape of the vaginal portion 320.

Loop 344 may be operatively coupled to vaginal portion 320. For example, lead 340 may be anchored within vaginal portion 320 at anchor 346 during the manufacturing process. For example, vaginal portion 320 may have two small openings at proximal end 326, the openings being configured to receive first end 348 and a second end 349 of lead 340. First end 348 and a second end 349 of lead 340 may be anchored to vaginal portion 320 using heat or glue for example. In some embodiments, anchor 346 may be in the form a reinforcement point to prevent lead 340 from breaking off of fertility device 300. For example, in the case where lead 340 is manufactured separately from vaginal portion 320, anchor 346 may be in the form of a ball (or other shape) that fits snugly within vaginal portion 320 to prevent lead 340 from breaking off. In other cases, where fertility device is manufactured as an integral unit, a reinforcement point may be created at anchor 346 during manufacturing (e.g., injection molding or 3D printing).

Figure 4:
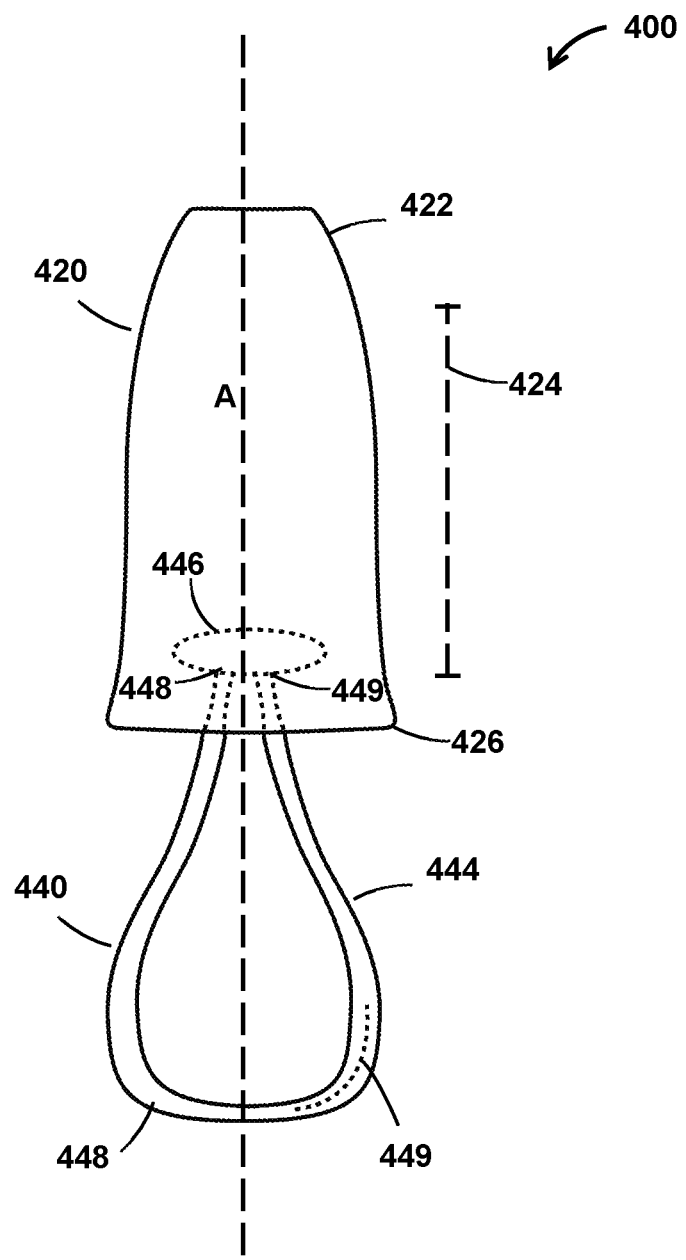
FIG. 4 is a hidden line plan view that illustrates an example fertility device, in accordance with some embodiments.

FIG. 4 depicts an example of fertility plug 400 according to some embodiments. In this example, vaginal portion 420 has a relatively circular cylindrical shape. In some embodiments, vaginal portion 420 includes a distal end 422, and a proximal end 424 (proximal to lead 440) opposite distal end 422 along an axis A. In some embodiments, distal end 422 has a relatively rounded tapered shape to facilitate insertion into the vagina. In some embodiments, vaginal portion 420 is coupled to lead 440 at proximal end 426. In some cases, vaginal portion 420 and lead 440 are constructed as an integral unit. In some cases, vaginal portion 420 and lead 440 are configured to be operatively coupled together. In some embodiments, vaginal portion 420 may have a diameter ranging between about 2 and about 2.5 cm. In some embodiments, proximal end has a slightly larger diameter that the diameter of the cylinder forming the vaginal portion 420. The vaginal portion 420 tapers slightly from proximal and towards middle section 424 and distal end 422. For example, vaginal portion may have a main portion 424 having a diameter of about 0.7 inches (or about 2 cm.) Distal end 422 is slightly rounded to facilitate insertion. Proximal end 426 has a slightly larger diameter of about one inches (or about 2.5 cm.) Fertility device 400 may be held in place for periods of time (spanning from minutes to hours) to help prevent the sperm from leaking from the vagina and increase the chances of the sperm reaching the uterus for fertilization.

In some embodiments, lead 440 may be the same or similar to lead 140, or 340 described above. In some embodiments, lead 440 is anchored within vaginal portion 420 at anchor 427. In some embodiments, lead 440 forms a loop 444 having a first end 448 and a second end 449. Loop 444 extends from end 448 (located near proximal end 426 of vaginal portion 420) to end portion 447 (also located near proximal end 426 of vaginal portion 420). Lead 440 is configured to facilitate removal of fertility device 400 from the vagina by providing loop 444 that acts like a handle for an easy grip and pull action. In some embodiments, lead 440 may be formed from the same material as vaginal portion 420 (e.g., silicone, latex, rubber, polycarbonate, methyl methacrylate, polyurethanes, glass, acrylic, plastic, or any combination thereof). In some embodiments, lead 440 and vaginal portion are manufactured as an integral unit (e.g., using injection molding, or 3D printing.) In some embodiments, lead 440 may be operatively coupled to vaginal portion 420. In some embodiments, lead 440 may be formed using a thread (e.g., reinforced cotton, nylon, satin, or polypropylene thread).

Lead 440 is configured to remain outside the vagina when fertility device 400 is placed in the vagina. Lead 440 is expected to be comfortable for the user to keep for extended periods of time. For example, after intercourse, fertility device 400 may be placed into the vagina while the woman is lying down (to prevent the sperm from leaving the vagina before inserting the fertility device). That said, the woman may be in different positions (e.g., having a lower back support, having her knees or legs raised close to her chest, to elevate her vagina or other positions). In some embodiments, The woman may place one or more finger through loop or handle 444) to guide fertility device into her vagina. In some cases, the handle (loop 444) may allow the woman to adjust position of fertility device during or after insertion (e.g., to a comfortable position.) In some embodiments, when placed in the woman's vagina, lead 440 remains at least partially outside the woman's body to help remove fertility device 400. While "wearing" fertility device 400, the woman is expected to be able to do her daily activities without interruption (e.g., showering, working, exercising, etc.) Lead 440 (when made from supple material) is small and discrete enough to be worn under clothing for example. In some embodiments, the woman may remove the fertility device from her vagina by placing one or more fingers through loop (handle) 444 of lead 440 and pulling fertility device 400 out of her vagina. As explained above, fertility device 400 may be washed with water and soap and stored away in most cases.

FIG. 5 describes an example of fertility plug 500 according to some embodiments. In this example, vaginal portion 520 has a relatively spherical shape. In some embodiments, vaginal portion 520 includes a distal end 522, and a proximal end 526 (proximal to lead 540) opposite distal end 522 along an axis A. In some embodiments, vaginal portion 520 is coupled to lead 540 at proximal end 526. In some cases, vaginal portion 520 and lead 540 are constructed as an integral unit. In some cases, vaginal portion 520 and lead 540 are configured to be operatively coupled together. In some embodiments, vaginal portion 520 has a diameter ranging between about two and about three cm.

In some embodiments, lead 540 includes an elongated portion 544 and an end portion 148. Elongated portion 544 extends from proximal end 526 of vaginal portion 520 to end portion 548. Lead 540 is configured to facilitate removal of fertility device 500 from the vagina by applying a pulling force to lead 540. In some embodiments, lead 540 may be formed from the same material as vaginal portion 520 (e.g., silicone, latex, rubber, polycarbonate, methyl methacrylate, polyurethanes, glass, acrylic, plastic, or any combination thereof). In some embodiments, lead 540 and vaginal portion are manufactured as an integral unit (e.g., using injection molding, or 3D printing.)

Figure 6:
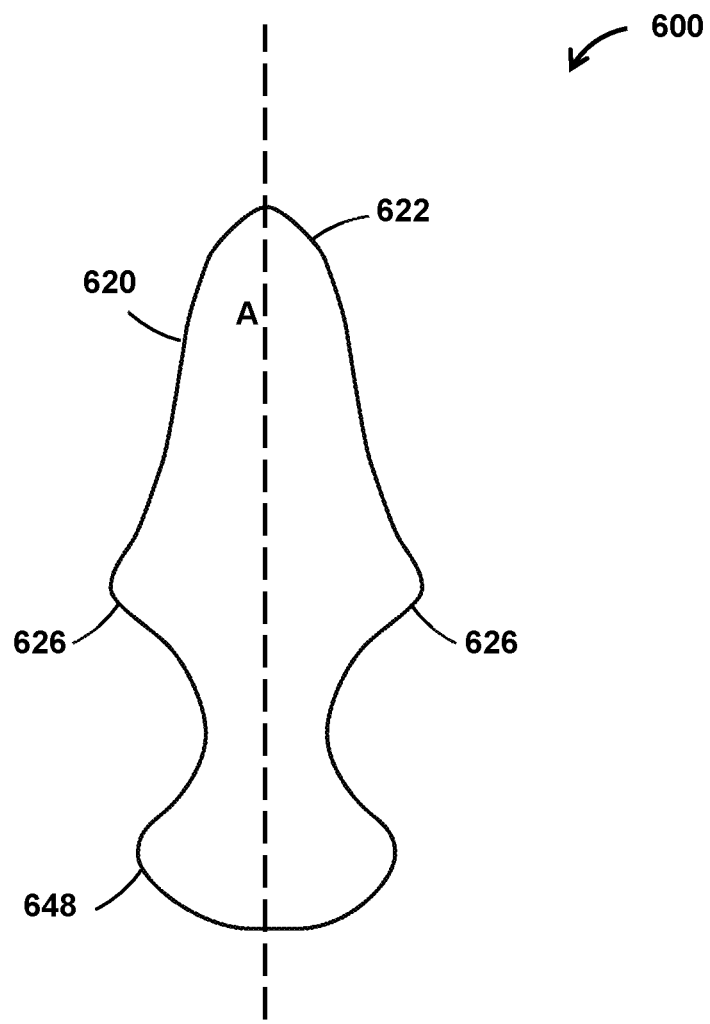
FIG. 6 is a hidden line plan view that illustrates an example fertility device, in accordance with some embodiments.

FIG. 6 describes an example of fertility plug 600 according to some embodiments. In this example, fertility plug 600 includes a vaginal portion 620 having a relatively pear shape. Vaginal portion 620 has a distal end 622 and a proximal end 626. Vaginal portion 620 tapers from proximal end 626 towards end 622 which is rounded for easy insertion. In some embodiments, vaginal portion 620 tapers from proximal end 626 and curves inward towards handle 648. In some cases, handle 648 may have a spherical shape with a diameter of about 2 cm. In some cases, handle 648 may have a pear shape having a diameter of about two cm at its widest section. In some embodiments, handle 648 may have a donut shape (or a ring shape) having a hollow portion for one or more finger to be inserted there through.

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to costs constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. It is to be understood that the present disclosure contemplates that, to the extent possible, one or more features of any embodiment can be combined with one or more features of any other embodiment. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. As used throughout this application geometric terms should be read as "substantially" having the shape and are not limited to platonic ideas.

The present techniques will be better understood with reference to the following enumerated embodiments:

1. A fertility device configured to be placed into a subject's vagina after intercourse, the fertility device comprising: a vaginal portion, the vaginal portion comprising: a proximal end; a distal end opposite the proximal end along a longitudinal axis; and a middle portion between the proximal and the distal end; and a lead operatively coupled to the proximal end, wherein: when at least part of the middle portion is placed into a subject's vagina, the lead remains partially outside the vagina, and the vaginal portion impedes leakage of sperm.
2. The device of embodiment 1, wherein the vaginal portion and the lead are relatively flexible.
3. The device of any of embodiments 1-2, wherein the vaginal portion is rotationally symmetrical about the longitudinal axis.
4. The device of any of embodiments 1-3, wherein the vaginal portion has an ellipsoidal shape, and wherein the vaginal portion tapers from the middle portion towards the proximal end and tapers from the middle portion towards the distal portion.
5. The device of any of embodiments 1-4, wherein the vaginal portion further comprises:
    an anchor at least partially inside the vaginal portion, wherein the lead is operatively coupled to the vaginal portion at the anchor.
6. The device of any of embodiments 1-5, wherein the lead further comprises a reinforcing filament.
7. The device of any of embodiments 1-6, wherein the lead comprises an elongated portion, and an end portion on an opposite side of the proximal end along the elongated portion, wherein the end portion forms a volume shape, and wherein the end portion facilitate placing and removing the fertility device from the vagina.
8. The device of embodiment 7, wherein the end portion forms a ring shape, the ring being configured to facilitate placing and removing the fertility device from the vagina.
9. The device of any of embodiments 1-8, wherein the lead comprises a top portion operatively connected to the proximal end of the vaginal portion, wherein the lead forms a loop, and wherein the lead loops such that the top portion is operatively coupled to the proximal end of the vaginal portion, and wherein the loop provides a handle to facilitate placing and removal of the fertility device from the vagina.
10. The device of any of embodiments 1-9, wherein the device is integrally manufactured from medical grade silicone.
11. The device of embodiment 10, wherein the device consists essentially of medical grade silicon.
12. The device of any of embodiments 1-11, wherein the vaginal portion tapers from the proximal end and curves inward towards the lead, and wherein the lead forms a spherical shape configured to provide a handle.
13. The device of any of embodiments 1-12, wherein the vaginal portion is configured to prevent leakage of sperm.
14. The device of any of embodiments 1-13, wherein the lead has a relative cross sectional area that is smaller than a relative cross sectional area of the vaginal portion.
15. A fertility device configured to be placed into a subject's vagina after intercourse, the fertility device comprising: a vaginal portion, the vaginal portion comprising: a proximal end; a distal end opposite the proximal end along a longitudinal axis; and a middle portion between the proximal and the distal end; and a means for facilitating insertion of at least part of the middle portion into a subject's vagina, wherein the means for facilitation is operatively coupled to the proximal end, and wherein the vaginal portion impedes leakage of sperm.
16. A fertility device configured to be placed into a subject's vagina after intercourse, the fertility device comprising: a means for impeding leakage of the sperm from a subject's vagina; and a lead operatively coupled to the means for impeding, wherein when at least part of the means for impeding is placed into the subject's vagina, the lead remains partially outside the vagina.
17. A method for impeding leakage of sperm from a subject's vagina after intercourse, the method comprising: obtaining a fertility device comprising: a vaginal portion, the vaginal portion comprising: a proximal end; a distal end opposite the proximal end along a longitudinal axis; and a middle portion between the proximal and the distal end; and a lead operatively coupled to the proximal end of the vaginal portion; and placing the vaginal portion at least partially inside the vagina such that the lead remains partially outside the vagina, and such that the vaginal portion impedes sperm from leaking out of the vagina.
18. The method of embodiment 17, further comprising: providing a pulling force to the lead; and removing the fertility device from the vagina.
19. The method of any of embodiments 17-18, further comprising applying a medicine on an outer surface of the device.
20. A method for impeding leakage of sperm for a subject's vagina after intercourse using a fertility device, the method comprising: receiving an insertion force parallel to a longitudinal axis of the device; moving into a subject's vagina along the longitudinal axis; applying a force radially outward to widen a path in the vagina; receiving a counteracting force acting radially inward from the vagina; holding itself static with a friction force acting in a longitudinal direction; and impeding semen from traveling out of the vagina.

What is claimed is:
1. A device configured to be placed into a subject's vagina after intercourse, the device comprising:
    a vaginal portion, the vaginal portion comprising:
        a proximal end;
        an anchor at least partially inside the vaginal portion;
        a distal end opposite the proximal end along a longitudinal axis; and
        a middle portion between the proximal and the distal end; and
    a lead operatively coupled to the vaginal portion at the anchor, wherein:

at least part of the vaginal portion, including at least the distal end, is configured to be placed into a subject's vagina after intercourse and impede semen flow from the vagina; and at least part of the lead is configured to remain at least partially outside the vagina when at least part of the vaginal portion is placed into the subject's vagina; and wherein the vaginal portion and the lead are both part of a single monolithic body.

2. The device of claim 1, wherein the lead is more flexible than the vaginal portion when subject to a bending force perpendicular to the longitudinal axis.

3. The device of claim 1, wherein the vaginal portion is rotationally symmetrical about the longitudinal axis.

4. The device of claim 1, wherein the vaginal portion has an ellipsoidal shape, and wherein the vaginal portion tapers from the middle portion towards the proximal end and tapers from the middle portion towards the distal-end.

5. The device of claim 1, wherein the lead houses an embedded reinforcing filament, wherein the entire embedded reinforcing filament is located in the monolithic body.

6. The device of claim 1, wherein the lead comprises an elongated portion, and an end portion on an opposite side of the proximal end along the elongated portion, wherein the end portion has a cross sectional area that monotonically decreases along the longitudinal axis, and wherein the end portion is configured to facilitate placing and removing the fertility device from the vagina.

7. The device of claim 5, wherein the monolithic body is molded around the embedded filament.

8. The device of claim 6, wherein the end portion forms a ring shape, the ring being configured to facilitate placing and removing the fertility device from the vagina.

9. The device of claim 1, wherein the lead comprises a top portion operatively connected to the proximal end of the vaginal portion, wherein the lead forms a loop, and wherein the lead loops such that the top portion is operatively coupled to the proximal end of the vaginal portion, and wherein the loop is configured to serve as a handle to facilitate placing and removal of the fertility device from the vagina.

10. The device of claim 1, wherein the device is integrally manufactured from medical grade silicone.

11. The device of claim 10, wherein the fertility device consists essentially of medical grade silicone.

12. The device of claim 1, wherein the vaginal portion tapers from the proximal end and curves inward towards the lead, and wherein the lead forms a spherical shape configured to provide a handle.

13. The device of claim 1, wherein the vaginal portion is configured to prevent leakage of sperm.

14. The device of claim 1, wherein the lead has a cross sectional area that is smaller than a cross sectional area of the vaginal portion.

15. The device of claim 1, comprising:
means for facilitating insertion of at least part of the middle portion into a subject's vagina.

16. The device of claim 1, comprising:
means for impeding leakage of sperm from a subject's vagina.

17. The device of claim 1, wherein the monolithic body is formed as an integral unit using a single mold cavity.

18. The device of claim 1, wherein the vaginal portion comprises an internal cavity.

19. The device of claim 1, wherein at least part of the vaginal portion is texturized.

20. The device of claim 1, wherein the device is washable and reusable.

21. The device of claim 1, further comprising:
an embedded reinforcing filament inside the lead;
a handle formed by an end portion of the lead; and
an internal cavity inside the vaginal portion;
wherein the device consists essentially of washable and reusable silicone.

22. A device configured to be placed into a subject's vagina after intercourse, the device comprising:
a vaginal portion, the vaginal portion comprising:
a proximal end;
a distal end opposite the proximal end along a longitudinal axis; and
a middle portion between the proximal and the distal end; and
a lead operatively coupled to the proximal end, wherein:
at least part of the vaginal portion, including at least the distal end, is configured to be placed into a subject's vagina after intercourse and impede semen flow from the vagina,
the lead houses an embedded reinforcing filament; and
at least part of the lead is configured to remain at least partially outside the vagina when at least part of the vaginal portion is placed into the subject's vagina; and
wherein the vaginal portion and the lead are both part of a single monolithic body and the entire embedded reinforcing filament is located in the monolithic body.

23. A device configured to be placed into a subject's vagina after intercourse, the device comprising:
a vaginal portion, the vaginal portion comprising:
a proximal end;
a distal end opposite the proximal end along a longitudinal axis; and
a middle portion between the proximal and the distal end; and
a lead operatively coupled to the proximal end, wherein:
at least part of the vaginal portion, including at least the distal end, is configured to be placed into a subject's vagina after intercourse and impede semen flow from the vagina,
the lead houses an embedded reinforcing filament; and
at least part of the lead is configured to remain at least partially outside the vagina when at least part of the vaginal portion is placed into the subject's vagina; and
wherein the vaginal portion and the lead are both part of a single monolithic body and the monolithic body is molded around the embedded filament.

24. A device configured to be placed into a subject's vagina after intercourse, the device comprising:
a vaginal portion, the vaginal portion comprising:
a proximal end;
a distal end opposite the proximal end along a longitudinal axis; and
a middle portion between the proximal and the distal end; and
a lead operatively coupled to the proximal end, wherein:
at least part of the vaginal portion, including at least the distal end, is configured to be placed into a subject's vagina after intercourse and impede semen flow from the vagina,
the lead houses an embedded reinforcing filament; and
at least part of the lead is configured to remain at least partially outside the vagina when at least part of the vaginal portion is placed into the subject's vagina;

an embedded reinforcing filament inside the lead;
an anchor at least partially inside the vaginal portion, wherein the lead is operatively coupled to the vaginal portion by the anchor;
a handle formed by an end portion of the lead; and
an internal cavity inside the vaginal portion;
wherein:
the device consists essentially of washable and reusable silicone; and
the vaginal portion and the lead are both part of a single monolithic body and the monolithic body is molded around the embedded filament.

* * * * *